United States Patent
Grobe, III et al.

(10) Patent No.: US 6,200,626 B1
(45) Date of Patent: Mar. 13, 2001

(54) SURFACE-TREATMENT OF SILICONE MEDICAL DEVICES COMPRISING AN INTERMEDIATE CARBON COATING AND GRAFT POLYMERIZATION

(75) Inventors: George L. Grobe, III; Paul L. Valint, Jr., both of Pittsford; Daniel M. Ammon, Jr., Rochester; Joseph A. McGee, Dewitt, all of NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/315,912

(22) Filed: May 20, 1999

(51) Int. Cl.[7] .............................. A61L 27/00; H05H 1/00; B05D 3/04
(52) U.S. Cl. ..................... 427/2.24; 427/488; 427/539; 427/169
(58) Field of Search ................... 427/2.24, 2.1, 427/488, 534, 535, 539, 164, 299, 393.5

(56) References Cited

U.S. PATENT DOCUMENTS

| | | |
|---|---|---|
| 4,055,378 | 10/1977 | Feneberg et al. ............... 351/160 |
| 4,122,942 | 10/1978 | Wolfson ........................ 206/5.1 |
| 4,143,949 | 3/1979 | Chen ............................ 351/160 |
| 4,214,014 | 7/1980 | Hoffer et al. ................. 427/40 |
| 4,312,575 | 1/1982 | Peyman et al. ................ 351/160 |
| 4,632,844 | 12/1986 | Yanagihara et al. ........... 427/38 |
| 4,673,584 * | 6/1987 | Nygren et al. ................ 427/407.2 |
| 4,731,079 * | 3/1988 | Stoy ............................ 623/6 |
| 5,007,928 * | 4/1991 | Okamura et al. .............. 427/491 |
| 5,206,298 | 4/1993 | Kawaguchi .................... 525/283 |
| 5,260,093 | 11/1993 | Kamel et al. .................. 427/2 |
| 5,658,561 * | 8/1997 | Nakabayashi et al. ......... 424/78.37 |
| 5,789,461 * | 8/1998 | Nicolson et al. .............. 427/2.24 |
| 5,805,264 | 9/1998 | Janssen et al. ................ 351/160 |
| 6,043,328 * | 3/2000 | Domschke et al. ............ 526/279 |

FOREIGN PATENT DOCUMENTS

| | | | |
|---|---|---|---|
| 0 157 212A2 | 3/1985 | (EP) .............................. | C23C/16/26 |
| WO 95/04609 | 2/1995 | (EP) . | |
| WO 94 06485 | 3/1994 | (WO) .......................... | A61L/27/00 |
| WO 94/29756 | 12/1994 | (WO) . | |

OTHER PUBLICATIONS

Koujiyundo Kaagaku Kenkyusho:KK Futaki Takehiko Formation of Plasma Polymerized Film, No. 01230777 Sep. 14, 1989 ; Sep. 3, 1988 No. 63055597.

Patents Abstracts of Japan, C23C 16/26, Applicant: Koujiyundo Kaagaku Kenkyusho:KK, Inventor: Futaki Takehiko, Title: Formation of Plasma Polymerized Film, Publication Number: 01230777, Publication Date: Sep. 14, 1989, Application Date: Sep. 3, 1988, Application Number: 63055597.

* cited by examiner

*Primary Examiner*—Shrive Beck
*Assistant Examiner*—Jennifer Kolb
(74) *Attorney, Agent, or Firm*—Robert B. Furr, Jr.

(57) ABSTRACT

The present invention provides an optically clear, hydrophilic coating upon the surface of a silicone medical device by sequentially subjecting the surface of the lens to plasma polymerization reaction in a hydrocarbon atmosphere to form a carbon layer, and then graft polymerizing a mixture of monomers comprising hydrophilic monomers onto the carbon layer. The invention is especially useful for forming a biocompatible coating on silicone hydrogel contact lenses.

21 Claims, No Drawings

SURFACE-TREATMENT OF SILICONE MEDICAL DEVICES COMPRISING AN INTERMEDIATE CARBON COATING AND GRAFT POLYMERIZATION

FIELD OF THE INVENTION

The present invention is directed toward the surface-treatment of medical devices such as contact lenses and medical implants. In particular, the present invention is directed to a method of modifying the surface of a medical device to increase its biocompatibility or hydrophilicity by coating the device with a polymerized carbon layer followed by graft polymerization onto the carbon layer by free-radical polymerization of a mixture of monomers to form a hydrophilic polymeric secondary coating over the carbon layer. The present invention is also directed to a contact lens or other medical device having such a surface coating.

BACKGROUND

Contact lenses made from silicone-containing materials have been investigated for a number of years. Such material can generally be subdivided into two major classes: hydrogels and non-hydrogels. Non-hydrogels do not absorb appreciable amounts of water, whereas hydrogels can absorb and retain water in an equilibrium state. Hydrogels generally have a water content greater than about five weight percent and more commonly between about ten to about eighty weight percent. Regardless of their water content, both non-hydrogel and hydrogel silicone contact lenses tend to have relatively hydrophobic, non-wettable surfaces.

Those skilled in the art have long recognized the need for rendering the surface of contact lenses hydrophilic or more hydrophilic. Increasing the hydrophilicity of the contact-lens surface improves the wettability of the contact lenses with tear fluid in the eye. This in turn improves the wear comfort of the contact lenses. In the case of continuous-wear lenses, the surface is especially important. The surface of a continuous-wear lens must be designed, not only for comfort, but to avoid adverse reactions such as corneal edema, inflammation, or lymphocyte infiltration.

Silicone lenses have been subjected to plasma surface-treatment to improve their surface properties, for example, in order to make the surface more hydrophilic, deposit-resistant, scratch-resistant, and the like. Examples of common plasma surface treatments include subjecting contact lens surfaces to a plasma comprising: (1) an inert gas or oxygen as, for example, in U.S. Pat. Nos. 4,055,378; 4,122942; and 4,214,014; (2) various hydrocarbon monomers as, for example, U.S. Pat. No. 4,143,949; and (3) combinations of oxidizing agents and hydrocarbons, for example, water and ethanol as in WO 95/04609 and U.S. Pat. No. 4,632,844. Sequential plasma surface treatments are also known, such as those comprising a first treatment with a plasma of an inert gas or oxygen, followed by a hydrocarbon plasma. For example, U.S. Pat. No. 4,312,575 to Peyman et al. discloses a process for providing a barrier coating on a silicone or polyurethane lens wherein the lens is subjected to an electrical glow discharge (plasma) involving a hydrocarbon atmosphere followed by oxygen in order to increase the hydrophilicity of the lens surface.

With oxidizing plasma, for example $O_2$ (oxygen gas), water, hydrogen peroxide, air, or the like, the plasma tends to etch the surface of the lens, creating radicals and oxidized functional groups. When used as the sole surface treatment, such oxidation renders the surface of a silicone lens more hydrophilic. However, the coverage of such surface treatment may not be complete and the bulk properties of the silicone materials may remain apparent at the surface of the lens, (e.g., silicone molecular chains adjacent the lens surface are capable of rotating thus exposing hydrophobic groups to the outer surface). Such coatings have been found to be thin, whereas thicker coatings tend to crack. Hydrocarbon plasmas, on the other hand, deposit a thin carbon layer (e.g. from a few Angstroms to several thousand Angstroms thick) upon the surface of the lens, thereby creating a barrier between the underlying silicone materials and the outer lens surface. Following deposition of a thin carbon layer on the lens to create a barrier, plasma oxidation can be employed to increase the hydrophilicity of the surface.

Although known surface treatments can be effective in improving the surface properties of non-hydrogel silicone contact lenses, problems are encountered when such treatments are applied to hydrogel lens. Silicone hydrogel lenses are coated in an unhydrated state, but subsequently hydrated during manufacture and prior to use. This hydration causes the lens to dramatically swell, commonly from about ten to about twenty percent in volume, depending upon the water content of the lens. Such swelling of the lens commonly may cause plasma coatings to crack, delaminate, and/or rub off. Furthermore, plasma coatings can compromise lens hydration by not permitting proper lens expansion and thereby causing lens destruction.

Various patents disclose the grafting of hydrophilic or otherwise biocompatible polymers to the surface of a contact lens in order to render the lens more biocompatible. For example, U.S. Pat. No. 5,805,264 to Jannsen et al. teaches the graft polymerization of an ethylenically unsaturated oligomer or polymer onto the surface of a lens in the presence of a cross-linking agent, following the plasma treatment of the lens to form hydroperoxy groups on the surface of the lens. U.S. Pat. No. 5,260,093 to Kamel et al. discloses covalently grafting a polymeric biocompatible material to the surface of a substrate by radio frequency plasma induction. U.S. Pat. No. 5,206,298 to Kawaguchi discloses the graft polymerization of 2-hydroxyethyl methacrylate by using a polymeric polymerization initiator comprising a peroxyfumurate.

The graft copolymerization onto a silicone substrate material has been problematic and unsatisfactory for several reasons. One serious complication has been the simultaneous and undesired homopolymerization of the vinylic monomer being grafted, resulting in wasted polymer that must be removed and discarded. Another problem has been the depth and density control of the graft. Grafts of excessive depth, grafts of insufficient density to achieve the desired property modification, and the swelling and degradation of the medical-device substrate during the process has occurred. Graft polymerization into interior portions of the substrate beneath the surface of the substrate can cause distortion of the medical device.

In view of the above, it would be desirable to find an improved optically clear, hydrophilic coating for the surface of a silicone hydrogel contact lens or other medical device that does not suffer from the aforementioned disadvantages and which is economical to produce. It would be further desirable to obtain a coating for a contact lens or other medical device that is more comfortable or biocompatible for longer periods of time, which coating, in the case of a contact lens, is simultaneously tear-wettable and highly permeable to oxygen. It would be desirable if such a biocompatibilized lens was capable of continuous wear overnight, preferable for a week or more without adverse effects to the cornea.

SUMMARY OF THE INVENTION

The present invention is directed toward surface treatment of silicone-contact lenses and other silicon-containing medical devices, including a method of modifying the surface of a contact lens to increase its hydrophilicity or wettability. The surface treatment comprises coating the device with a carbon layer, followed by graft polymerization of a hydrophilic polymer onto the surface of the carbon layer. In a preferred embodiment, a contact lens surface is pretreated with an oxidizing plasma prior to deposition of the carbon layer, in order to improve adhesion of the carbon layer. The present invention is also directed to a medical device comprising a surface made by such a method.

DETAILED DESCRIPTION OF THE INVENTION

As stated above, the present invention is directed toward surface treatment of silicone medical devices, including contact lenses, intraocular lenses and vascular implants, to improve their biocompatibility. By the term silicone, it is meant that the material being treated is an orgalnic polymer comprising at least five percent by weight silicone (—OSi— linkages), preferably 10 to 100 percent by weight silicone, more preferably 30 to 90 percent by weight silicone. The present invention is especially advantageous for application to contact lenses, either silicone hydrogels or silicone rigid-gas-permeable materials. The invention is especially advantageous for silicone hydrogel continuous-wear lenses. Hydrogels are a well-known class of materials, which comprise hydrated, cross-linked polymeric systems containing water in an equilibrium state. Silicone hydrogels generally have a water content greater than about five weight percent and more commonly between about ten to about eighty weight percent. Such materials are usually prepared by polymerizing a mixture containing at least one silicone-containing monomer and at least one hydrophilic monomer. Either the silicone-containing monomer or the hydrophilic monomer may function as a cross-linking agent (a cross-linker being defined as a monomer having multiple polymerizable finctionalities) or a separate cross-linker may be employed. Applicable silicone-containing monomeric units for use in the formation of silicone hydrogeln are well known in the art and numerous examples are provided in U.S. Pat. Nos. 4,136,250; 4,153,641; 4,740,533; 5,034,461; 5,070,215; 5,260,000; 5,310,779; and 5,3513,995.

Examples of applicable silicon-containing monomeric units include bulky polysiloxanylalkyl (meth)acrylic: monomers. An example of bulky polysiloxanylalkyl (meth)acrylic monomers is represented by the following Formula 1:

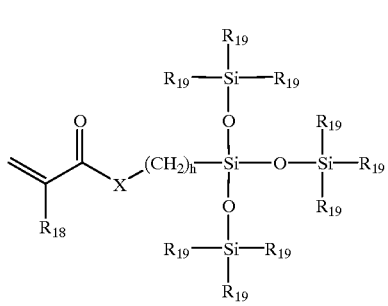

(I)

wherein:

X denotes —O— or —NR—;

each $R_{18}$ independently denotes hydrogen or methyl;

each $R_{19}$ independently denotes a lower alkyl radical, phenyl radical or a group represented by

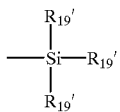

wherein each $R_{19}'$ independently denotes a lower alkyl or phenyl radical; and h is 1 to 10.

Some preferred bulky monomers are methacryloxypropyl tris(trimethyl-siloxy)silane or tris(trimethylsiloxy) silylpropyl methacrylate, sometimes referred to as TRIS and tris(trimethylsiloxy)silylpropyl vinyl carbamate, sometimes referred to as TRIS-VC.

Such bulky monomers may be copolymerized with a silicone macromonomer, which is a poly(organosiloxane) capped with an unsaturated group at two or more ends of the molecule. U.S. Pat. No. 4,153,641 to Deichert et al. discloses, for example, various unsaturated groups, including acryloxy or metbacryloxy.

Another class of representative silicone-containing monomers includes silicone-containing vinyl carbonate or vinyl carbamate monomers such as: 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy) silane]; 3-[tris(trimethylsiloxy)silyl] propyl vinyl carbamate; 3-[tris(trimethylsiloxy)silyl] propyl allyl carbamate; 3-[tris(trimethylsiloxy)silyl]propyl vinyl carbonate; t-butyldimethylsiloxyethyl vinyl carbonate; trimethylsilyl-ethyl vinyl carbonate; and trimethylsilylmethyl vinyl carbonate.

Another class of silicon-containing monomers includes polyurethane-polysiloxane macromonomers (also sometimes referred to as prepolymers), which may have hard-soft-hard blocks like traditional urethane elastomers. Examples of silicone urethanes are disclosed in a variety or publications, including Lai, Yu-Chin, "The Role of Bulky Polysiloxanylalkyl Methacryates in Polyurethane-Polysiloxane Hydrogels," *Journal of Applied Polymer Science*, Vol. 6C, 1193–1199 (1996). PCT Published Application No. WO 96/31792 discloses examples of such monomers, which disclosure is hereby incorporated by reference in its entirety. Further examples of silicone urethane monomers are represented by Formulae II and III:

(II)

or

(III)

wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, at cycloalkyl diradical, an alkyl cycloalkyl diradical, an aryl diradical or an alkylaryl diradical having 1 to 40 carbon atoms and which may contain ether, thio or amine linkages in the main chain;

\* denotes a urethane or ureido linkage;

a is at least 1;

A denotes a divalent polymeric radical of Formula IV:

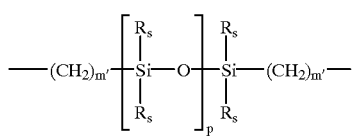

(IV)

wherein:
each Rs independently denotes an alkyl or fluoro-substituted alkyl group having 1 to 10 carbon atoms which may contain ether linkages between carbon atoms;

m' is at least 1; and p is a number that provides a moiety weight of 400 to 10,000;

each of E and E' independently denotes a polymerizable unsaturated organic radical represented by Formula VI:

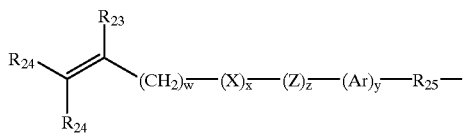

(VI)

wherein:
$R_{23}$ is hydrogen or methyl;

$R_{24}$ is hydrogen, an alkyl radical having 1 to 6 carbon atoms, or a —CO—Y—$R_{26}$ radical wherein Y is —O—, —S— or —NH—;

$R_{25}$ is a divalent alkylene radical having 1 to 10 carbon atoms;

$R_{26}$ is a alkyl radical having 1 to 12 carbon atoms;

X denotes —CO— or —OCO—;

Z denotes —O— or —NH—;

Ar denotes an aromatic radical having 6 to 30 carbon atoms;

w is 0 to 6; x is 0 or 1; y is 0 or 1; and z is 0 or 1.

A preferred silicone-containing urethane monomer is represented by Formula (VII):

wherein m is at least 1 and is preferably 3 or 4, a is at least 1 and preferably is 1, p is a number which provides a moiety weight of 400 to 10,000 and is preferably at least 30, $R_{27}$ is a diradical of a diisocyanate after removal of the isocyanate group, such as the diradical of isophorone diisocyanate, and each E" is a group represented by:

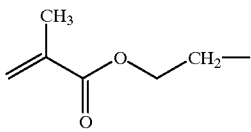

Another class of representative silicone-containing monomers includes fluorinated monomers. Such monomers have been used in the formation of fluorosilicone hydrogels to reduce the accumulation of deposits on contact lenses made therefrom, as described in U.S. Pat. Nos. 4,954,587, 5,079,319 and 5,010,141. The use of silicone-containing monomers having certain fluorinated side groups, i.e. —($CF_2$)—H, have been found to improve compatibility between the hydrophilic and silicone-containing monomeric units, as described in U.S. Pat. Nos. 5,387,662 and 5,321,108.

In one preferred embodiment of the invention, a silicone hydrogel material comprises (in bulk, that is, in the monomer mixture that is copolymerized) 5 to 50 percent, preferably 10 to 25, by weight of one or more silicone macromonomers, 5 to 75 percent, preferably 30 to 60 percent, by weight of one or more polysiloxanylalkyl (meth) acrylic monomers, and 10 to 50 percent, preferably 20 to 40 percent, by weight of a hydrophilic monomer. Examples of hydrophilic monomers include, but are not limited to, ethylenically unsaturated lactam-containing monomers such as N-vinyl pyrrolidinone, methacrylic and acrylic acids; acrylic substituted alcohols, such as 2-hydroxyethylmethacrylate and 2-hydroxyethylacrylate and acrylamides, such as methacrylamide and N,N-dimethylacrylamide, vinyl carbonate or vinyl carbamate monomers such as disclosed in U.S. Pat. Nos. 5,070,215, and oxazolinone monomers such as disclosed in U.S. Pat. No. 4,910,277. Other hydrophilic monomers will be apparent to one skilled in the art.

The above silicone materials are merely exemplary, and other materials for use as substrates that can benefit by being coated according to the present invention have been disclosed in various publications and are being continuously developed for use in contact lenses and other medical devices.

The subject method utilizes standard plasma oxidation and deposition processes (also referred to as "electrical glow discharge processes") to provide a thin, durable surface upon

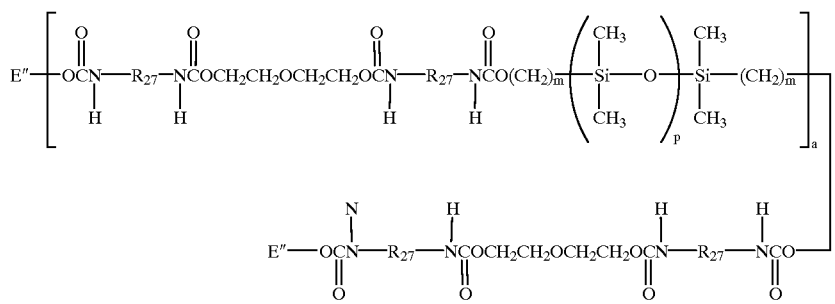

the medical device preliminary to the covalently bonded grafting of a hydrophilic polymeric coating. Examples of such plasma processes are provided in U.S. Pat. Nos. 4,143,949; 4,312,575; and 5,464,667.

Although such processes are well known in the art, a brief overview is provided below. Plasma surface treatments involve passing an electrical discharge through a gas at low pressure. The electrical discharge may be at radio frequency (typically 13.56 MHz), although microwave and other frequencies can be used. Electrical discharges produce ultraviolet (UV) radiation, in addition to being absorbed by atoms and molecules in their gas state, resulting in energetic, electrons and ions, atoms (ground and excited states), molecules and radicals. Thus, a plasma is a complex mixture of atoms and molecules in both ground and excited states, which reach a steady state after the discharge is begun. The circulating electrical field causes these excited atoms and molecules to collide with one another as well as the walls of the chamber and the surface of the material being treated.

The deposition of a coating from a plasma onto the surface of a material has been shown to be possible from high-energy plasmas without the assistance of sputtering (sputter-assisted deposition). Monomers can be deposited from the gas phase and polymerized in a low pressure atmosphere (0.005 to 5 torr, preferably 0.01 to 1.0 torr) onto a substrate utilizing continuous or pulsed plasmas, suitably as high as about 1000 watts. A modulated plasma, for example, may be applied 100 milliseconds on then off. In addition, liquid nitrogen cooling has been utilized to condense vapors out of the gas phase onto a substrate and subsequently use the plasma to chemically react these materials with the substrate. However, plasmas do not require the use of external cooling or heating to cause the desired deposition. Low or high wattage (5 to 1000, preferably 20–500 watts) plasmas can coat even the most chemical-resistant substrates, including silicones.

In one embodiment of thie present invention, which will be described in terms of a contact lens although also applicable to silicon medical devices in general, the method sequentially comprises:

(a) subjecting the oxidized surface of the lens to a plasma-polymerization deposition with an C1 to C10 saturated or unsaturated hydrocarbon to form a polymeric carbonaceous primary coating (or "carbon layer") on the lens surface; and (b) grafting a mixture of monomers (inclusive of macromers) onto the carbon layer by free-radical polymerization of the monomers to form a hydrophilic, biocompatible secondary coating.

Preferably, step (a) is preceded by subjecting the surface of the medical device to a plasma oxidation reaction so as to more effectively bond the polymerized hydrocarbon coating to the lens in order to resist delamination and/or cracking of the surface coating from the lens upon lens hydration. It has been found that by subjecting the untreated silicone hydrogel lens material to plasma prior to subsequent plasma polymerization (e.g. deposition of a carbon layer), the surface of the lens is prepared to better bind the hydrocarbon plasma that is subsequently deposited on the lens. Thus, for example, if the lens is ultimately made from a hydrogel material that is hydrated (wherein the lens typically expands by ten to about twenty percent), the coating remains intact and bound to the lens, providing a more durable coating which is resistant to delamination and/or cracking. In step (a) then, a thin hydrocarbon coating is deposited on the lens, which is necessary to provide for more complete coverage of the underlying silicone material. In step (b), the carbon surface is exposed to, and reacted with, mixture of monomers under free-radical polymerization conditions, resulting in a hydrophilic polymer coating attached to the carbon surface, rendering the carbon coating of step (a) hydrophilic.

As mentioned above, it is preferred to initially oxidize the surface of the lens; for example, a silicone hydrogel continuous-wear lens is initially oxidized by the use of an oxidation plasma to render the subsequent hydrocarbon deposition more adherent to the lens. Such an oxidation of the lens may be accomplished in an atmosphere composed of an oxidizing media. It is preferred that a relatively "strong" oxidizing plasma is utilized in this oxidation, for example. ambient air drawn through a five percent (5%) hydrogen peroxide solution. For example, plasma oxidation may be carried out at an electric discharge frequency of 13.56 Mhz, preferably between about 20 to 500 watts at a pressure of about 0.1 to 1.0 torr, preferably for about 10 seconds to about 10 minutes or more, more preferably about 1 to 10 minutes. The contact lens can alternatively be pretreated by providing an aminated surface by subjecting said object to an ammonia or an aminoalkane plasma. Those skilled in the art will know other methods of improving or promoting adhesion for bonding of the subsequent carbon layer. For example, plasma with an inert gas will also improve bonding. It would also be possible to deposit a silicon-containing monomer to promote adhesion.

In step (a), after the preferred but optional plasma-oxidation surface treatment, the lens surface is subjected to a plasma polymerization reaction in a hydrocarbon atmosphere to form a polymeric surface on the lens. Any hydrocarbon capable of polymerizing in a plasma environment may be utilized; however, the hydrocarbon must be in a gaseous state during polymerization and have a boiling point below about 200° C. at one atmosphere. Preferred hydrocarbons include aliphatic compounds having from 1 to about 15 carbon atoms, including both saturated and unsaturated aliphatic compounds. Examples include, but are not limited to, C1 to C15, preferably C1 to C10 alkanes, alkenes, or alkynes such as methane, ethane, propane, butane, pentane, hexane, ethylene, propylene, butylene, cyclohexane, pentene, acetylene. Also, C1 to C8 aromatics such as benzene, styrene, methylstyrene, and the like may be employed. As is known in the art, such hydrocarbon groups may be unsubstituted or substituted so long as they are capable of forming a plasma. Various combinations of iifferent hydrocarbons may also be used.

The use of C1 to C4 hydrocarbons for the purpose of carbon-coating substrates is advantageous for its controllability in terms of thickness, deposition rate, hardness, etc. However, with respect to hydrogcl materials, the C4 to C8 hydrocarbons. (for example, butane, butene, isobutylene, and 1,3-butadiene) are preferred, at least with respect to hydrogel-forming substrates, due to the relative less flexibility of coatings made from C1 to C3 hydrocarbons such as methane. Such coatings may suffer during the expansion of the hydrogel substrate in water or saline and are more prone to cracking, which is less desirable. The use of longer carbcn chains in the deposition plasma gas results in coatings that are more flexible. The longer carbon chain coatings have been found to be more expandable, especially when coating hydrogel substrates in saline or water.

It has been found that, at least with respect to silicone hydrogels, the use of diolefins such as 1,3-butadiene or isoprene are particularly preferred, resulting in coatings that are more flexible and expandable in water. More flexible coatings are especially preferred for "high-water" lenses that expand considerably upon hydration.

The hydrocarbon coating can be deposited from plasma, for example, in a low-pressure atmosphere (about 0.001 to 5 torr) at a radio frequency of 13.56 Mhz, at about 10 to 1000 watts, preferably 20–4,00 watts in about 30 seconds to 10 minutes or more, more preferably 30 seconds to 3 minutes. Other plasma conditions may be suitable as will be understood by the skilled artisan., for example, using pulsed plasma.

If the hydrocarbon coating provided is too thick, it can cause a haziness, resulting in a cloudy lens. Furthermore, excessively thick coatings can interfere with lens hydration due to differences in expansion between the lens and the coating, causing the lens to rip apart. Therefore, the thickness of the hydrocarbon layer should be less than about 500 Angstroms, preferably between about 25 and 500 Angstroms, more preferably 50 to 200 Angstroms, as determined by XPS analysis.

To graft the polymer coating to the carbon layer, an initiator may be employed to cause ethylenically-unsaturated monomers (including macromers) to react with the surface. In any case, the carbon layer must be rendered reactive (activated) to promote the covalent attachment of the polymer to the surface. One advantage of the use of diolefins to form the carbon layer is that unsaturated sites for the initiation of graft polymerization are already present When employing other hydrocarbons to form the carbon layer, an activator or initiator may be empolyed to speed the free-radical graft polymerization of the surface. Alternately, conventional techniques for the initiation of graft polymerization may be applied to the carbon layer to create peroxy or other functional groups that can also initiate graft polymerization. For example, it has been known in the art that various vinylic monomers can be graft polymerized onto polymer substrates which have been first treated with ionizing radiation in the presence of oxygen or with ozone to form peroxy groups on the surface of said substrate. See U.S. Pat. Nos. 3,008,920 and 3,070,573, for instance, for ozonization of the substrate. Alternatively, a carbon layer formed by plasma may already contain radicals that when exposed to air, form peroxide groups that decompose to oxygen radicals. Additional plasma/corona treatment is also capable of forming radicals for reaction with ethylenically-unsaturated monomers or polymers. Still another way to promote graft polymerization is to plasma treat the substrate, for example with argon or helium in plasma form, to form free radicals on its outmost surfaces, then contacting these radicals with oxygen to form hydroperoxy groups from the free radicals, followed by graft polymerizing ethylenically unsaturated monomers onto the surface.

The grafting polymer may be formed by using an aqueous solution of the ethylenically unsaturated monomer or mixture of monomers capable to undergoing graft addition polymerization onto the surface of the substrate. In those cases where one or more of the monomers is not appreciably soluble in water, a cosolvent such as tert-butyl alcohol may be used to enhance the solubility of the monomer in the aqueous graft polymerization system.

The graft polymer may be the reaction product of a mixture of monomers comprising one or more hydrophilic monomers. The optional presence of some hydrophobic monomers may also be used to impart desired properties such as resistance to lipid or protein deposition.

In one embodiment of the invention, an activated material or medical device such as a contact lens can be dipped in a monomer solution comprising at least one hydrophilic monomer (the term "monomer" is herein inclusive of "macromers," also referred to as "macromonomers").

Preferably the mixture of monomers comprise 1 to 100 mole percent of hydrophilic monomeric units, preferably 50 to 100 mole percent, more preferably 60 to 100 mole percent. As indicated above, other monomeric units which are hydrophobic optionally may also be used in amounts up to 35 mole percent, preferably 0 to 20 mole percent, most preferably 0 to 10 mole percent. Examples of hydrophobic monomers are alkyl methacrylate, fluorinated alkyl methacrylates, long-chain acrylaamides such as octyl acrylamide, and the like. Hydrophilic monomers may be aprotic types such as acrylamides (N,N-dimethylacrylamide, DPAA), lactams such as N-vinylpyrrolidinone, and poly(alklylene oxides) such as methoxypolyoxyethylene methacrylates, or may be protic types such as methacrylic acid or hydroxyalkyl methacrylates such as hydroxyethyl methacrylate. Hydrophilic monomers may also include zwitterions such as N,N-dimethyl-N-methacryloxyethyl-N-(3-sulfopropyl)-ammonium betain (SPE) and N,N-dimethyl-N-methacrylamidopropyl-N-(3-sulfopropyl)-ammonium betain (SPP). Macromers useful in this invention include, for example, those described in U.S. Pat. No. 5,525,691 and 5,177,165 to Valint and McGee.

Suitable hydrophilic monomers for comprising the hydrophilic reactive polymers include generally water soluble conventional vinyl monomers such as acrylates and methacrylates of the general structure:

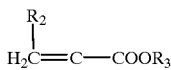

where $R_2$ is hydrogen or methyl and $R_3$ is hydrogen or is an aliphatic hydrocarbon group of up to 10 carbon atoms substituted by one or more water solubilizing groups such as carboxy, hydroxy, amino, lower alhylamino, lower dialkyamino, a polyethylene oxide group with from 2 to about 100 repeating units, or substituted by one or more sulfate, phosphate sulfonate, phosphonate, carboxamido, sulfonamido or phosphonamido groups, or mixtures thereof;

Preferably $R_3$ is an oligomer or polymer such as polyethylene glycol, polypropylene glycol, poly(ethylene-propylene) glycol, poly(hydroxyethyl methacrylate), poly(dimethyl acrylamide), poly(acrylic acid), poly(methacrylic acid), polysulfone, poly(vinyl alcohol), polyacrylamide, poly(acrylamide-acrylic acid) poly(styrene sulfonate) sodium salt, poly(ethylene oxide), poly(ethylene oxide-propylene oxide), poly(glycolic acid), poly(lactic acid), poly(vinylpyrrolidone), cellulosics, polysaccharides, mixtures thereof, and copolymers thereof;

acrylamides and methacrylamides of the formula

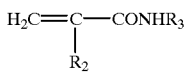

where $R_2$ and $R_3$ are as defined above;

acrylamides and methacrylamides of the formula

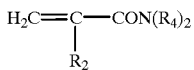

where R4 is lower alkyl of 1 to 3 carbon atoms and $R_2$ is as defined above;

maleates and furmarates of the formula:

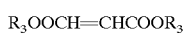

wherein $R_3$ is as defined above;

vinyl ethers of the formula $$H_2C=CH-O-R_3$$

where $R_3$ is as defined above;

aliphatic vinyl compounds of the formula $$R_2CH=CHR_3$$

where $R_2$ is as defined above and $R_3$ is as defined above with the provise that $R_3$ is other than hydrogen; and vinyl substituted heterocycles, such as vinyl pyridines, piperidines and imidazoles and N-vinyl lactams, such as N-vinyl-2-pyrrolidone.

Included among the usefull water soluble monomers are: 2-hydroxyethyl-; 2- and 3-hydroxypropyl-; 2,3-dihydroxypropyl-; polyethoxyethyl-; and polyethoxypropylacrylates, methacrylates, acrylamides and methacrylamides; acrylamide, methacrylamide, N-methylacrylamide, N-methylmethacrylamide, N,N-dimethylacrylamide, N,N-dimeth,ylmethacrylamide, N,N-dimethyl- and N,N-diethylaminoethyl acrylate and methacrylate and the corresponding acrylamides and methacrylamides; 2-and 4-vinylpyridine; 4-and 2-methyl-5-vinylpyridine; N-methyl-4-vinylpiperidine; 2-methyl-1-vinylimidazole; N,-N-dimethylallylamine; dimethylaminoethyl vinyl ether; N-vinylpyrrolidone; acrylic and methacrylic acid; itaconic, crotonic, fumaric and maleic acids and the lower hydroxyalkyl mono and diesters thereof, such as the 2-hydroxethyl fumarate and maleate, sodium acrylate and methacrylate; 2-methacryloyloxyethylsulfonic acid and allylsulfonic acid.

Suitable hydrophobic copolymerizable monomers include water insoluble conventional vinyl monomers such as acrylates and methacrylates of the general formula $$H_2C=\overset{R_2}{\underset{|}{C}}-COOR_5$$

where $R_2$ is as defined above and $R_5$ is a straight chain or branched aliphatic, cycloaliphatic or aromatic group having up to 20 carbon atoms which is unsubstituted or substituted by one or more alkoxy, alkanoyloxy or alkyl of up to 12 carbon atoms, or by halo, especially chloro or preferably fluoro, C2 to C5 polyalkyleneoxy of 2 to about 100 units, or an oligomer such as polyethylene, poly(methyl methacrylate), poly(ethyl methacrylate), or poly(glycidyl methacrylate), mixtures thereof, and copolymers thereof;

acrylamides and methacylaraides of the general formula $$H_2C=\overset{R_2}{\underset{|}{C}}-CONHR_5$$

where $R_2$ and $R_5$ are defined above, vinyl ethers of the formula $$H_2C=CH-O-R_5$$

where $R_5$ is as defined above;

vinyl esters of the formula $$H_2C=CH-OCO-R_5$$

where $R_5$ is as defined above;

maleates and fumarates of the formula $$R_5OOC-HC=CH-OOOR_5$$

where $R_5$ is as defined above; and vinylic substituted hydrocarbons of the formula $$R_2CH=CHR_5$$

where $R_2$ and $R_5$ is as defined above

Suitable hydrophobic monomers include, for example: methyl, ethyl, propyl, isopropyl, butyl, ethoxyethyl, methoxyethyl, ethoxypropyl, phenyl, benzyl, cyclohexyl, hexafluoroisopropyl, or n-octyl-acrylates and methacrylates as well as the corresponding acrylamides and methacrylamides; dimethyl fumarate, dimethyl maleate, diethyl fumarate, methyl vinyl ether, ethoxyethyl vinyl ether, vinyl acetate, vinyl propionate, vinyl benzoate, acrylonitrile, styrene, alpha-methylstyrene, 1-hexene, vinyl chloride, vinyl methylketone, vinyl stearate, 2-hexene and 2-ethylhexyl methacrylate.

The graft polymerization is typically carried out in the presence of a solvent. Determination of reactivity ratios for copolymerization are disclosed in Odian, *Principles of Polymerization*, 2nd Ed., John Wiley & Sons, p. 425–430 (1981), the disclosure of which is incorporated by reference herein. In a preferred method according to the present invention, the carbon-coated contact lens or other medical device may be exposed to graft polymerization by immersing the substrate in a solution containing the polymers. For example, a contact lens may be placed or dipped for a suitable period of time in a solution of the reactive monomers in a suitable medium, for example, an aprotic solvent such as acetonitrile. Suitable solvents are in principle all solvents which dissolve the monomer used, for example water: alcohols such as lower alkanols, for example, ethanol and methanol; carboxamides such as dimethylformamide; dipolar aprotic solvents such as dimethyl sulfoxide or methyl ethyl ketone; ketones such as acetone or cyclohexanone; hydrocarbons such as toluene; ethers such as THF, dimethoxyethane or dioxane; halogenated hydrocarbons such as trichloroethane, and also mixtures of suitable solvents, for example mixtures of water and an alcohol, for example a water/ethanol or water/methanol mixture.

To promote the free-raclical grafting, the substrate may optionally be immersed in a first solution containing an initiator followed by a immersion of the the substrate in a second solution containing the inonomer mixture. Typical polymerization initiators include free-radical-generating polymerization initiators of the type illustrated by acetyl peroxide, lauroyl peroxide, decanoyl peroxide, coprylyl peroxide, benzoyl peroxide, tertiary butyl peroxypivalate, sodium percarbonate, tertiary butyl peroctoate, and azobisisobutyronitrile (AIBN). Ultraviolet free-radical initiators illustrated by diethoxyacetophenone can also be used. The curing process will of course depend upon the initiator used and the physical characteristics of the comonomer mixture such as viscosity. If an initiator is employed, it is typically present at a level within the range of 0.01 to 2 weight percent of the mixture of monomers. A mixture of the above-mentioned monomers may be warmed with addition of a free-radical former.

The hydrophilic reactive polymers are attached to silicone medical devices which may be made by conventional manufacturing processes. For example, contact lenses for application of the present invention can be manufactured employing various conventional techniques, to yield a shaped article having the desired posterior and anterior lens surfaces. Spincasting methods are disclosed in U.S. Pat. Nos. 3,408,429 and 3,660,545; preferred static casting methods are disclosed in U.S. Pat. Nos. 4,113,224 and 4,197,266. Curing of the monomeric mixture is often followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

After producing a lens having the desired final shape, it is desirable to remove residual solvent from the lens before edge-finishing operations. This is because, typically, an organic diluent is included in the initial monomeric mixture in order to minimize phase separation of polymerized products produced by polymerization of the monomeric mixture and to lower the glass transition temperature of the reacting polymeric mixture, which allows for a more efficient curing process and ultimately results in a more uniformly polymerized product. Sufficient uniformity of the initial monomeric mixture and the polymerized product are of particular concern for silicone hydrogels, primarily due to the inclusion of silicone-containing monomers which may tend to separate from the hydrophilic comonomer. Suitable organic diluents include, for example, monohydric alcohols, with $C_6$–$C_{10}$ straight-chained aliphatic monohydric alcohols such as n-hexanol and n-nonanol being especially preferred; diols such as ethylene glycol; polyols such as glycerin; ethers such as diethylene glycol monoethyl ether; ketones such as methyl ethyl ketone; esters such as methyl enanthate; and hydrocarbons such as toluene. Preferably, the organic diluent is sufficiently volatile to facilitate its removal from a cured article by evaporation at or near ambient pressure. Generally, the diluent is included at five to sixty percent by weight of the monomeric mixture, with ten to fifty percent by weight being especially preferred.

The cured lens is then subjected to solvent removal, which can be accomplished by evaporation at or near ambient pressure or under vacuum. An elevated temperature can be employed to shorten the tiviie necessary to evaporate the diluent. The time, temperature and pressure conditions for the solvent removal step will vary depending on such factors as the volatility of the diluent and the specific monomeric components, as can be readily determined by one skilled in the art. According to a preferred embodiment, the temperature employed in the removal step is preferably at least 50° C., for example, 60 to 80° C. A series of heating cycles in a linear oven under inert gas or vacuum may be used to optimize the efficiency of the solvent removal. The cured article after the diluent removal step should contain no more than twenty percent by weight of diluent, preferably no more than five percent by weight or less.

Following removal of the organic diluent, the lens is next subjected to mold release and optional machining operations. The machining step includes, for example, buffing or polishing a lens edge and/or surface. Generally, such machining processes may be performed before or after the article is released from a mold part. Preferably, the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

Subsequent to the mold release/machining operations, the lens is subjected to surface treatment according to the present invention, as described above, including the plasma polymerization to form a carbon layer and the subsequent graft polymerization of a hydrophilic polymer onto the carbon layer.

Plasma treatment involves passing an electrical discharge through a gas at low pressure, preferably at radio frequency (typically, 13.56 MHz). As mentioned above, this electrical discharge is absorbed by atoms and molecules in their gas state, thus forming a plasma that interacts with the surface of the contact lens.

After initiation by a low energy discharge, collisions between energetic free electrons present in the plasma cause the formation of ions, excited molecules, and free-radicals. Such species, once formed, can react with themselves in the gas phase as well as with further ground-state molecules. The plasma treatment may be understood as an energy dependent process involving energetic gas molecules. For chemical reactions to take place at the surface of the lens, one needs the required species (element or molecule) in terms of charge state and particle energy. Radio frequency plasmas generally produce a distribution of energetic species. Typically, the "particle energy" refers to the average of the so-called Boltzman-style distribution of energy for the energetic species. In a low-density plasma, the electron energy distribution can be related by the ratio of the electric field strength sustaining the plasma to the discharge pressure (E/p). The plasma power density P is a fuinction of the wattage, pressure, flow rates of gases, etc., as will be appreciated by the skilled artisan. Background information on plasma technology, hereby incorporated by reference, includes the following: A. T. Bell, Proc. Intl. Conf. Phenom. Ioniz. Gases, "*Chemical Reaction in Nonequilibrium Plasmas*", 19–33 (1977); J. M. Tibbitt, R. Jensen, A. T. Bell, M. Shen, Macromolecules, "*A Modelfor the Kinetics of Plasma Polymerization*", 3, 648–653 (1977); J. M. Tibbitt, M. Shen, A. T. Bell, J. Macromol. Sci.-Chem., "*Struotural Characterization of Plasma-Polymerized Hydrocarbons*", A10, 1623–1648 (1976); C. P. Ho, H. Yasuda, J. Biomed. Mater. Res., "*Ultrathin coating of plasma polymer of methane applied on the surface of silicone contact lenses*", 22, 919–937 (1988); H. Kobayashi, A. T. Bell, M. Shen, Macromolecules, "*Plasma Polymerization of Saturated and Unsaturated Hydrocarbons*", 3, 277–283 (1974); R. Y. Chen, U.S. Pat. No. , 4,143,949, Mar. 13, 1979, "*Process for Putting a Hydrophilic Coating on a Hydrophobic Contact lens*"; and H. Yasuda, H. C. Marsh, M. O. Bumgarner, N. Morosoff, J. of Appl. Poly. Sci., "*Polymerization of Organic Compounds in an Ele-troless Glow Discharge. VI. Acetylene with Unusual Co-monomers*", 19, 2845–2858 (1975).

Based on this previous work in the field of plasma technology, the effects of changing pressure and discharge power on the rate of plasma modification can be understood. The rate generally decreases as the pressure is increased. Thus, as pressure increases the value of E/p, the ratio of the electric field strength sustaining the plasma to the gas pressure decreases and causes a decrease in the average electron energy. The decrease in electron energy in turn causes a reduction in the rate coefficient of all electron-molecule collision processes. A further consequence of an increase in pressure is a decrease in electron density. Providing that the pressure is held constant, there should be a linear relationship between electron density and power.

In practice, contact lenses are surface-treated by placing them, in their unhydrated state, within an electric glow discharge reaction vessel (e.g., a vacuum chamber). Such reaction vessels are commercially available. The lenses may be supported within the vessel on an aluminum tray (which acts as an electrode) or with other support devices designed to adjust the position of the lenses. The use of a specialized support devices which permit the surface treatment of both sides of a lens are known in the art and may be used in the present invention.

Subsequent to the plasma processing of the lens, the carbon coated lens are immersed in a solution containing the monomer mixture comprising hydrophilic monomers, as mentioned above. The Examples below provide the Applicants' best mode for forming the coating on a silicone lens or other medical device.

Subsequent to surface treatment, the lens may be subjected to extraction to remove residuals in the lenses. Generally, in the manufacture of contact lenses, some of the monomer mix is not fully polymerized. The incompletely polymerized material from the polymerization process may affect optical clarity or may be harmful to the eye. Residual material may include solvents not entirely removed by the previous solvent removal operation, unreacted monomers from the monomeric mixture, oligomers present as by-products from the polymerization process, or even additives that may have migrated from the mold used to form the lens.

Conventional methods to extract such residual materials from the polymerized contact lens material include extraction with an alcohol solution for several hours (for extraction of hydrophobic residual material) followed by extraction with water (for extraction of hydrophilic residual material). Thus, some of the alcohol extraction solution remains in the polymeric network of the polymerized contact lens material, and should be extracted from the lens material before the lens may be worn safely and comfortably on the eye. Extraction of the alcohol from the lens can be achieved by employing heated water for several hours. Extraction should be as complete as possible, since incomplete extraction of residual material from lenses may contribute adversely to the useful life of the lens. Also, such residuals may impact lens performance and comfort by interfering with optical clarity or the desired uniform hydrophilicity of the lens surface. It is important that the selected extraction solution in no way adversely affects the optical clarity of the lens. Optical clarity is subjectively understood to be the level of clarity observed when the lens is visually inspected.

Subsequent to extraction, the lens is subjected to hydration in which the lens is fully hydrated with water, buffered saline, or the like. When the lens is ultimately fully hydrated (wherein the lens typically may expand by 10 to about 20 percent or more), the coating remains intact and bound to the lens, providing a durable, hydrophilic coating which has been found to be resistant to delamination.

Following hydration, the lens may undergo cosmetic inspection wherein trained inspectors inspect the contact lenses for clarity and the absence of defects such as holes, particles, bubbles, nicks, tears. Inspection is preferably at 10X magnification. After the lens has passed the steps of cosmetic inspection, the lens is ready for packaging, whether in a vial, plastic blister package, or other container for maintaining the lens in a sterile condition for the consumer. Finally, the packaged lens is subjected to sterilization, which sterilization may be accomplished in a conventional autoclave, preferably under an air pressurization sterilization cycle, sometime referred to as an air-steam mixture cycle, as will be appreciated by the skilled artisan. Preferably the autoclaving is at 100° C. to 200° C. for a period of 10 to 120 minutes. Following sterilization, the lens dimension of the sterilized lenses may be checked prior to storage.

Objects and advantages of this invention are further illustrated by the following examples, but the particular materials and amounts thereof recited in these examples, as well as other conditions and details should not be construed at unduly limit this invention.

EXAMPLE 1

This example discloses a representative silicone hydrogel lens material used in the following Examples. Table 1 below provides the formulation a polyfumarate silicone hydrogel formulation used to make a lens substrate for later surface modification according to the present invention:

TABLE 1

| Component | Parts by Weight |
|---|---|
| $F_2D_{20}$ | 20 |
| TRIS | 40 |
| DMA | 40 |
| n-Hexanol | 5 |
| DAROCUR-1173 | 0.5 |
| IMVT | 150 ppm |

The following materials are designated above:
TRIS    tris(trimethylsiloxy)silyipropyl methacrylate
DMA    N,N-dimethylacrylamide
$F_2D_{20}$    a silicne-containing crosslinking resin as previously described in U.S. Pat. Nos. 5,374,662 and 5,496,871.
Darocur    a UV initiator
IMVT    a tint agent, namely 1,4-bis[4-(2-methacryloxyethyl) phenylamino] anthraquinone

EXAMPLE 2

This Example illustrates a typical process for preparing a contact lens prior to its surface modification according to Ihe present invention. Silicone hydrogel lenses made of the formulation of Example 1 above were cast molded from polypropylene molds. Under an inert nitrogen atmosphere, 45-$\mu$l of the formulation was injected onto a clean polypropylene concave mold half and covered with the complementary polypropylene convex mold half. The mold halves were compressed at a pressure of 70 psi, and the mixture was cured for about 15 minutes in the presence of UV light (6–11 mW/cm$^2$ as measured by a Spectronic UV melter). The mold was exposed to UV light for about five (5) additional minutes. The top mold half was removed and the lenses were maintained at 60° C. for three hours in a forced air oven to remove n-hexanol. Subsequently, the lens edges were ball buffed for ten seconds at 2300 rpm with a force of 60 g.

EXAMPLE 3

This example illustrates surface modification of a contact lens according to the present invention. The lenses were made from the formulation of Example 1 (silicone fumarate, 36% water upon hydration). A plasma chamber was prepumped to 0.01 torr, prior to plasma treatment of the lenses, from residual air in the chamber. The surface modification consisted of an initial oxidation plasma at 1.0 torr, 200 watts for five minutes in duration in an air/water/peroxide atmosphere (air drawn through a peroxide solution). Subsequently, the hydrocarbon coating (employing either methane or butadiene) was deposited at 150 watts for 5 min at 0.5 torr per side. Subsequent to the carbon coating, the surface was rendered hydrophilic by electrical surface treatment with a manual TANTEC LAB SYSTEM corona system. Samples were corona treated in air at atmospheric pressure. This process utilizes a maximum of 250 watts or a peak electrode voltage of 20,000 volts (AC peak @ 25 kHz). The corona produced a strong ozone smell. The conditions of the corona were level six with a three second treatment per side. The ½" (1.27 cm) ball electrode was held in the center of the coated lens ¼" (0.635 cm) from the surface. The surface of the polymer was completely water wet (HPLC grade water, 72.4 dynes/cm) after the corona treatment.

Carbon films greater than 100 Angstroms (transparent) thickness were deposited on the lens substrates. This deposition made use of a methane or butadiene gas which was accelerated and forced into the lens surfaces which caused a carbon deposit to form. The idea behind the deposition was to completely cover the substrate such that none of the underlying chemistry is visible over the outermost 100 Angstroms, the sampling depth of the XPS instrument). The carbon coating was an excellent substrate for the attachment of secondary coatings by graft polymerization. These secondary coatings were applied in one of two ways: (1) corona treatment for three seconds, followed by dipping onto a monomer solution and rinsing in water or saline followed by autoclaving; and (2) post-polymerization of a monomer to the surface of the butadiene utilizing an appropriate initiator and monomers.

A typical post-polymeri.zation surface-treatment was as follows: A solution of 0.1 mmole of a hydrophilic surface-active macromer (Compositions A–D in Table 2 below), 0.03 m mole Vazo-86 azo-initiator, and 100 ml of deoxygenated HPLC-grade water was prepared. Lenses treated with a butadiene plasma were placed in vials under a nitrogen atmosphere. The vials were filled with the aqueous solution, sealed and placed in an oven at 90° C. overnight. The lenses were rinsed with a large volume of purified water. Half the lenses were allowed to dry and the other half were placed in boiling water for four hours and then dried.

TABLE 2

| Composition | Composition | Concentration (mmoles per 100 ml) | Concentration (g/100 ml) | Solution |
|---|---|---|---|---|
| A | Fluoro/PVP (25/75) | 1 | 0.45 | Water |
| B | Fluoro/PVP (25/75) | 1.1 | 0.5 | Water |
| C | Fluoro/PEO 5K (80/20) | 1.1 | 0.7 | Water |
| D | Sulfo-Betain | 1.8 | 0.5 | Saline |

The structural formula for the polymer of Compositions A and B may be generalized as follows:

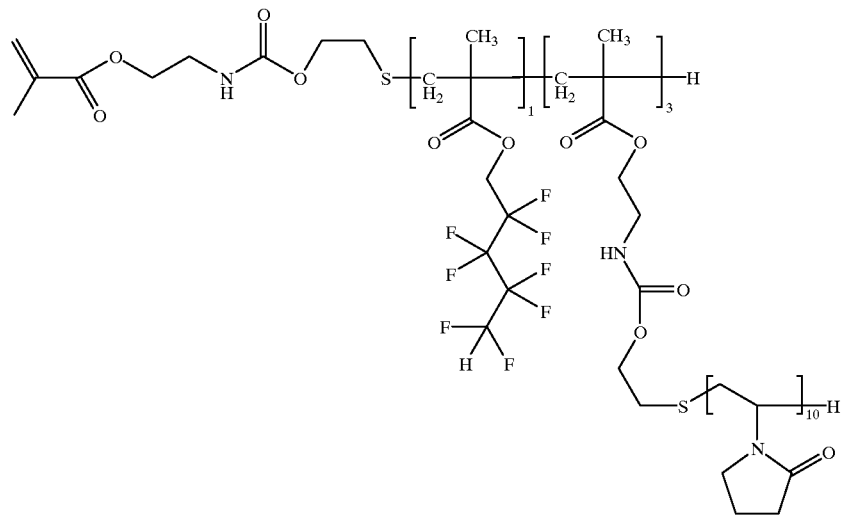

The structural formula for the polymer of Composition C may be generalized as follows:

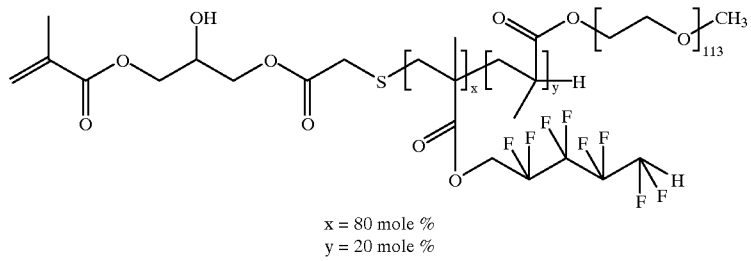

x = 80 mole %
y = 20 mole %

The structure of the sulfo-betain used in composition D was as follows:

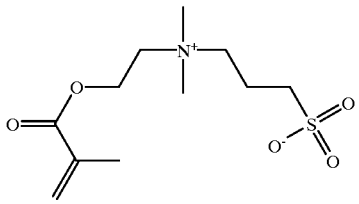

The lenses at each step of the process were analyzed by X-ray Photoelectron Spectroscopy (XPS), directly from the plasma chamber and after full processing as indicated below. All fully processed lenses were autoclaved in vials. The XPS data was obtained on a Physical Electronics [PHI] Model 5600. This instrument utilized a monochromatized Al anode operated at 300 watts, 15 kV and 20 milliamps. The base pressure of this instrument was $2.0 \times 10^{-10}$ torr while the pressure during operation was $5.0 \times 10^{-8}$ torr. This instrument used a hemispherical energy analyzer. The instrument had an Apollo workstation with PHI 8503A version 4.0A software. The practical measure of sampling depth for this instrument at a sampling angle of 45° was 74Å. Each specimen would be analyzed utilizing a low resolution survey spectra [0–1100 eV] to identify the elements present on the sample surface [10–100 Å]. High resolution spectra would be obtained on those elements detected from the low resolution survey scans. The elemental composition would be determined from the high resolution spectra. All data will be charged referenced to the carbon (CHx) peak at 285 eV. The atomic composition was calculated from the areas under the photoelectron peaks after sensitizing those areas with the instrumental transmission function and atomic cross sections for the orbital of interest. Since XPS does not detect the presence of hydrogen or helium, these elements will not be included in any calculation of atomic percentages.

The XPS analysis of the coated substrates appear below in Tables 3 and 4 below. This data reflects the atomic composition of the lenses analyzed over the top 74 Angstroms (relative to carbon1s electrons). These tables outline the attachment of the secondary coatings applied to methane and butadiene carbon surfaces. The butadiene surface was chemically more reactive to these secondary polymerization schemes than the methane carbon surface. The second method utilized to attach polymers utilized corona oxidation of a surface for the creation of free-radicals on the carbon surface for the attachment of a monomer, polymer and/or solvent to the carbon surface. Each side of the carbon-modified silicone hydrogel was modified via a three second corona. The corona-modified, carbon-coated silicone hydrogel substrates were then dipped into the polymer, monomer or solvent of choice. The graft polymers were attached to the surface as evidenced from the XPS data in Tables 3 and 4 below. The data also reveals how the modifications survive hydration and autoclaving.

TABLE 3

| Step | Description | Specimen | Fluorine | Oxygen | Nitrogen | Carbon | Silicon | CHx | C—O | OCO |
|---|---|---|---|---|---|---|---|---|---|---|
| 1 | As Received, Extracted | Average | 0.0 | 17.4 | 5.2 | 65.7 | 11.6 | 65.5 | 27.5 | 6.9 |
|  |  | STDEV | 0.0 | 0.1 | 0.1 | 0.8 | 0.8 | 0.8 | 1.1 | 0.4 |
| 2 | Oxidation and Methane | Average | 0.0 | 3.1 | 0.0 | 95.2 | 1.6 | 100.0 | 0.0 | 0.0 |
|  | Plasma | STDEV | 0.0 | 0.6 | 0.0 | 0.6 | 0.3 | 0.0 | 0.0 | 0.0 |
| 3 | Corona | Average | 0.0 | 22.5 | 1.5 | 74.7 | 1.4 | 76.5 | 11.2 | 12.2 |
|  | Oxidation (dry) or | STDEV | 0.0 | 1.9 | 0.6 | 1.3 | 0.6 | 3.7 | 3.0 | 1.1 |
|  | Corona | Average | 0.0 | 17.6 | 3.7 | 75.0 | 3.7 |  |  |  |
|  | Oxidation (wet) | STDEV | 0.0 | 1.4 | 1.5 | 4.2 | 2.4 |  |  |  |
| 4A | Monomer | Average | 0.1 | 24.7 | 4.1 | 66.3 | 4.8 | 44.1 | 47.7 | 8.2 |
|  | (HEMA) Dip | STDEV | 0.1 | 0.9 | 0.5 | 1.3 | 0.1 | 3.5 | 2.5 | 2.0 |
| 4B | Polymer (Fluor/PVP 25/95) | Average | 3.3 | 18.8 | 4.9 | 66.0 | 7.0 | 74.4 | 17.1 | 4.5 |
|  | Dip | STDEV | 2.8 | 1.3 | 0.7 | 2.3 | 2.9 | 2.4 | 1.5 | 2.9 |

TABLE 4

| Step | Description |  | F | O | N | C | Si |
|---|---|---|---|---|---|---|---|
| 1–2 | Oxidation and | Average | 0.0 | 8.7 | 0.6 | 90.7 | 0.1 |
|  | Butadiene Plasma | STDEV | 0.0 | 0.4 | 0.6 | 0.4 | 0.1 |
| 3A | Fluoro/PVP | Average | 11.5 | 19.6 | 5.7 | 61.1 | 2.1 |
|  | (25/75)/hydrated/ water | STDEV | 3.5 | 2.7 | 0.6 | 3.9 | 1.1 |
| 3B | Corona/Betain/ | Average | 4.1 | 22.1 | 6.3 | 62.9 | 2.0 |
|  | Hydrated | STDEV | 5.7 | 2.2 | 0.5 | 5.5 | 1.0 |
| 4A | Autoclaved | Average | 2.3 | 17.3 | 4.8 | 72.8 | 2.6 |
|  |  | STDEV | 0.6 | 0.8 | 0.7 | 1.4 | 1.4 |
| 4B | Autoclaved | Average | 2.3 | 17.3 | 4.8 | 72.8 | 2.6 |
|  |  | STDEV | 0.6 | 0.8 | 0.7 | 1.4 | 1.4 |

The X-ray Photoelectron Spectroscopy (XPS) data showed that the silicone hydrogel substrates were coated through a carbon deposit from a plasma gas-phase reaction. The coatings were primarily aliphatic carbon in composition with little to no oxygen (0.1–2.5% atomic composition). The plasmas employed in this example were typically high wattage (50–400 watts, although lower wattage is also possible), low pressure 0.1–1.0 torr, and varying amounts of time depending on the coating (composition and thickness) to be produced.

In addition, the morphology of the substrates was examined by Atomic Force Microscopy (AFM). The images of the methane plasma carbon-coated surface appear to be completely coated. Many of the features of the original substrate appear to be reproduced in the process of coating with the carbon. A problem arose when the hydrogel substrate was expanded in water, isopropyl alcohol or saline. The methane coating would crack when expanded. The edges of the carbon coating could be seen in the AFM images to delaminate from the expanded (10% expansion) silicone hydrogel. The edges of the carbon coating turned up in a curled fashion as if the coating was delaminating. However, when an oxygen plasma was utilized to increase the adhesion of the carbon coating, no delamination or edge curling was noted in the AFM images. Also, if the methane gas in the plasma chamber was replaced with butane, isobutylene or 1,3 butadiene, the coating would flex when the hydrogel matrix was expanded in water. The 1,3 butadiene may be expanded in excess of forty percent (40%) to completely crack and break the coating. The hardness of the coating can be varied via the thickness and the addition of hydrogen or helium to the base plasma gas. The coatings were determined to be transparent and did not either cosmetically or functionally degrade the performance of the lens when tested in vitro.

EXAMPLE 4

This example illustrates a surface modification of a contact lens according to the present invention employing further examples of monomer mixtures for graft polymerization. The lenses of Example 1 (silicone fumurate, 36% water upon hydration) were analyzed directly from the plasma chamber and after full processing as indicated below. All fully processed lenses were autoclaved in vials. Solution A, comprising N,N-dimethylacrylamide (DMA), was prepared by dissolving 3 grams of distilled DMA in 300 ml of purified water. Solution B was prepared by dissolving 2 g of DMA and 0.01 g of ethyleneglycol dimethacrylate (EGDMA) in 200 ml of purified water. Solution C was prepared by dissolving 1 g DMA. and 0.3 g of SPE (the betain in the previous example) in 100 ml of purified water. A solution of Vazo 64 0.2 percent (weight/volume, hereafter w/v) in ethanol was prepared and 200 µl was added to each lens vial. The redox catalyst pair was a 10 % (w/v) solution of ammonium persulfate and a 5 % (v/v) solution of tetramethylenediamine. A 50 µl portion of each solution were added to each lens sample. All treatments were carried out overnight. Sample vials were opened and the treatment solutions were replaced with Boiate Buffered Saline followed by one autoclave cycle.

Table 5 below gives sample numbers, corresponding treatments, and XPS data. Ten lenses were treated in each case. The lenses were extracted and dried prior to any treatment.

TABLE 5

| Sample Number | Plasma Treatment | Post Treatment | Catalyst | Temp. | Side (A or P) | O1s | N1s | C1s | Si2p | Na1s |
|---|---|---|---|---|---|---|---|---|---|---|
| 1 | NH2/Butadiene | DMA | None | 80° C. | A | 18 | 6.8 | 70.7 | 4.5 | 0 |
| 2 | NH2/Butadiene | DMA | None | 80° C. | A | 15.6 | 5.1 | 72.8 | 6.5 | 0.1 |
| 3 | NH2/Butadiene | DMA | None | 80° C. | P | 18.2 | 6.6 | 67.9 | 7 | 0 |
| 4 | NH2/Butadiene/O2 | DMA | None | 80° C. | A | 16.7 | 3.9 | 73.9 | 5.5 | 0 |
| 5 | NH2/Butadiene/O2 | DMA | None | 80° C. | A | 19.6 | 4.5 | 66 | 9.8 | 0.1 |
| 6 | NH2/Butadiene/O2 | DMA | None | 80° C. | P | 32.9 | 6.9 | 50.6 | 4.6 | 2.6 |
| 7 | NH2/Butadiene/O2 | DMA/EGDMA | None | 80° C. | A | 15.7 | 4.7 | 73.3 | 6.1 | 0.1 |
| 8 | NH2/Butadiene/O2 | DMA/EGDMA | None | 80° C. | A | 16.3 | 4.6 | 75 | 4 | 0 |
| 9 | NH2/Butadiene/O2 | DMA/EGDMA | None | 80° C. | P | 15.5 | 4.1 | 75.9 | 4.6 | 0.2 |
| 10 | NH2/Butadiene | DMA | Vazo 64 | 80° C. | A | 17.4 | 5.8 | 71.9 | 4.8 | 0.2 |
| 11 | NH2/Butadiene | DMA | Vazo 64 | 80° C. | A | 20.7 | 6.1 | 64.9 | 8.2 | 0.1 |
| 12 | NH2/Butadiene | DMA | Vazo 64 | 80° C. | P | 21.5 | 6.5 | 62.2 | 9.6 | 0.2 |
| 13 | NH2/Butadiene | DMA | Redox | R.T. | A | 14.5 | 7.1 | 77.3 | 0.9 | 0.2 |
| 14 | NH2/Butadiene | DMA | Redox | R.T. | A | 15.8 | 7.7 | 74.6 | 1.4 | 0.5 |
| 15 | NH2/Butadiene | DMA | Redox | R.T. | P | 16.7 | 5.5 | 70.5 | 7.3 | 0.1 |
| 16 | NH2/Butadiene | DMA/EGDMA | Redox | R.T. | A | 15.3 | 7.8 | 74 | 2.7 | 0.1 |
| 17 | NH2/Butadiene | DMA/EGDMA | Redox | R.T. | A | 18.5 | 7.6 | 71 | 2.1 | 0.9 |
| 18 | NH2/Butadiene | DMA/EGDMA | Redox | R.T. | P | 16.3 | 5.8 | 71.5 | 6.4 | 0 |
| 19 | NH2/Butadiene | DMA/SPE | Redox | R.T. | A | 18.9 | 7.2 | 69.8 | 3.5 | 0.1 |
| 20 | NH2/Butadiene | DMA/SPE | Redox | R.T. | A | 17.2 | 7.2 | 70.1 | 5.4 | 0.2 |
| 21 | NH2/Butadiene | DMA/SPE | Redox | R.T. | P | 18 | 5.4 | 68.1 | 8.2 | 0.2 |
| AA | NH2/Butadiene | None | None | R.T. | A (mean) | 4.86 | 1 | 93.1 | 1 | na |

TABLE 5-continued

| Sample Number | Plasma Treatment | Post Treatment | Catalyst | Temp. | Side (A or P) | O1s | N1s | C1s | Si2p | Na1s |
|---|---|---|---|---|---|---|---|---|---|---|
| AB | NH2/Butadiene | None | None | R.T. | P (mean) | 8.42 | 2.2 | 84.7 | 4.7 | na |
| BA | NH2/Butadiene/ O2 | None | None | R.T. | A (mean) | 19 | 3.4 | 74 | 3.3 | na |
| BB | NH2/Butadiene/ O2 | None | None | R.T. | P (mean) | 23.1 | 4.9 | 66.1 | 4.8 | na |

Many other modifications and variations of the present invention are possible in light of the teachings herein. It is therefore understood that, within the scope of the claims, the present invention can be practiced other than as herein specifically described.

What is claimed is:

1. A method for treating the surface of a silicone medical device comprising the steps of:
   (a) subjecting the surface of said silicone medical device to an oxidative plasma treatment;
   (b) subjecting the oxidatively plasma treated surface of the silicone medical device to a plasma polymerization reaction in a hydrocarbon atmosphere to foin a carbonaceous polymeric surface on the lens having a thickness of 50 to 500 Angstroms; and
   (c) grafting a mixture of polymerizable ethylenically unsaturated monomers comprising hydrophilic monomers onto the carbonaceous polymeric surface by means of a free-radical reaction, thus foiming a biocompatible surface on the medical device.

2. The method of claim 1, wherein the medical device is a silicone contact lens or in intraocular device.

3. The method of claim 1, wherein the medical device is a silicone hydrogel, continuous-wear contact lens.

4. The method of claim 1, wherein the plasma pretreatment comprises oxidation of the surface with an nitrogen or oxygen containing oxidizing gas.

5. The method of claim 4, wherein the plasma pretreatment is conducted at 10 to 1000 watts for a period of 1 to 10 minutes, at a pressure of 0.01 to 1.0 torr.

6. The method of claim 4, wherein the plasma pretreatment is conducted in an oxidizing atmosphere comprising a gas selected from at least one of: ambient air, oxygen gas, hydrogen peroxide, alcohol, water, and ammonia.

7. The method of claim 1, wherein the plasma polymerization reaction of step (b) is conducted in an atmosphere comprising hydrocarbons having 1 to 10 carbon atoms.

8. The method of claims 7 wherein the hydrocarbons are aliphatic or olefinic and comprise 4 to 8 carbon atoms.

9. The method of claim 8, wherein the hydrocarbons comprise at least one of butane, isobutylene, 1,3-butadiene, and isoprene.

10. The method of claim 1, wherein the hydrophilic monomers are macromonomers.

11. The method of claim 10, wherein the graft polymerization is conducted in the presence of an initiator on the surface of the carbonaceous polymeric surface of step (b).

12. The method of claim 1, wherein the monomer mixture comprises 10 to 100 mole percent of hydrophilic monomers selected from the group consisting of acrylamides, lactams, poly(alkyleneoxy)methacrylates, methacrylic acid or hydroxyalkyl methacrylates.

13. The method of claim 12, wherein the hydrophilic monomers are selected from the group consisting of dimethylacrylamide, acrylamide, hydroxyethyl methacrylate, and N-vinyl pyrrolidinone.

14. The method of claim 1, wherein the mixture of ethylenically unsaturated monomers comprises 0 to 20 mole percent hydrophobic monomers.

15. The method of claim 1, wherein the grafting step (c) comprises dipping the medical device in a solution comprising the mixture of ethylenically unsaturated monomers.

16. A device including a hydrophilic surface, wherein said surface comprises:
   (a) a first oxidized layer created by plasma treatment of the surface of the silicone medical device;
   (b) a second carbonaceous layer attached to the first oxidized layer (a); and
   (c) polymers grafted to the second carbonaceous layer (b) by means of free-radical graft polymerization, wherein said polymers arc derived from a mixture of monomers comprising hydrophilic monomers.

17. The medical device of claim 16, wherein the medical device is a silicone contact lens.

18. The medical device of claim 16, wherein the medical device is a silicone hydrogel continuous-wear lens.

19. The medical device of claim 16, wherein the monomer mixture comprises 10 to 100 mole percent of hydrophilic monomers selected from the group consisting of acrylamides, lactams, poly(alkyleneoxy)methacrylates, methacrylic acid or hydroxyalkyl methacrylates.

20. The medical device of claim 19, wherein the hydrophilic monomers are selected from the group consisting of dimethylacrylamide, acrylamide, hydroxyethyl methacrylate, and N-vinyl pyrrolidinone.

21. The method of claim 19, wherein the monomer mixture comprises 0 to 35 mole percent hydrophobic monomers.

* * * * *